(12) United States Patent
Royer

(10) Patent No.: US 6,869,976 B2
(45) Date of Patent: Mar. 22, 2005

(54) INORGANIC-POLYMER COMPLEXES FOR THE CONTROLLED RELEASE OF COMPOUNDS INCLUDING MEDICINALS

(75) Inventor: Garfield P. Royer, Upperville, VA (US)

(73) Assignee: Royer Biomedical, Inc., Frederick, MD (US)

( * ) Notice: Subject to any disclaimer, the term of this patent is extended or adjusted under 35 U.S.C. 154(b) by 0 days.

(21) Appl. No.: 10/365,419

(22) Filed: Feb. 13, 2003

(65) Prior Publication Data

US 2003/0170307 A1 Sep. 11, 2003

Related U.S. Application Data

(60) Division of application No. 09/509,016, filed as application No. PCT/US98/19528 on Sep. 26, 1998, which is a continuation-in-part of application No. 08/935,300, filed on Sep. 22, 1997, now Pat. No. 6,391,336.

(51) Int. Cl.[7] .................. A61K 38/14; A61K 31/7048; A61K 31/704; A61K 31/496
(52) U.S. Cl. .................. 514/772.3; 514/2; 514/937; 514/944; 514/8; 514/29; 514/37; 514/200; 514/54; 514/951; 424/426; 424/486; 424/409; 424/422; 424/501; 424/468; 536/23.5
(58) Field of Search .................. 514/772.3, 2, 937, 514/944, 8, 29, 37, 200, 54, 951; 424/426, 486, 409, 422, 501, 468; 536/23.5

(56) References Cited

U.S. PATENT DOCUMENTS

| | | |
|---|---|---|
| 4,946,870 A | 8/1990 | Partain, III. et al. |
| 5,385,887 A | 1/1995 | Yim et al. |
| 5,614,206 A | 3/1997 | Randolph et al. |
| 5,648,097 A | 7/1997 | Nuwayser |
| 5,697,922 A | 12/1997 | Thombre |
| 5,783,214 A | 7/1998 | Royer |
| 5,807,567 A | 9/1998 | Randolph et al. |
| 6,030,636 A | 2/2000 | Randolph et al. |
| 6,113,947 A | 9/2000 | Cleland et al. |
| 6,207,197 B1 | 3/2001 | Illum et al. |
| 6,245,351 B1 | 6/2001 | Nara et al. |

FOREIGN PATENT DOCUMENTS

| | | |
|---|---|---|
| EP | 642785 A2 | 3/1995 |
| EP | 0 642 785 A2 | 3/1995 |
| WO | 94/12152 A1 | 10/1993 |

OTHER PUBLICATIONS

Mackey et al, *Antibiotic Loaded Plaster of Paris Pellets: An In vitro Study of a Possible Method of Local Antibiotic Therapy in Bone Infection*, Clinical Orthopedics and Related Research, No. 167, Jul. 1982, pps. 263–268.

Stabile et al, *Development and Application of Antibiotic–Loaded Bone Cement Beads*, Journal of the American Podiatric Medical Association, vol. 80, No. 7, Jul. 1990, pps. 354–359.

Popham et al, *Antibiotic–Impregnated Beads—Part II: Factors in Antibiotic Selection*, Orthopaedic Review, vol. XX, No. 4, Apr. 1991, pps. 331–337.

Henry et al, *Antiobiotic–Impregnated Beads—Part I: Bead Implantation Versus Systemic Therapy*, Orthopaedic Review, vol. XX, No. 3, Mar. 1991, pps. 242–247.

Henry et al, *Antibiotic–Impregnated Beads: A Production Technique*, Contemporary Orthopaedics, vol. 19, No. 3, Sep. 1989, pps. 221–226.

Bowyer et al, *Antibiotic Release From Impregnated Pellets And Beads*, The Journal of Trauma, vol. 3, No. 3, Mar. 1994, pps. 331–335.

Torholm et al, *Total Hip Joint Arthroplasty with Gentamicin–Impregnated Cement*, Clinical Orthopaedics and Related Research, No. 181, Dec. 1983, pps. 99–106.

Goodell et al, *Preparation and Release Characteristics of Tobramycin–Impregnatd Polymethylmethacrylate Beads*, American Journal of Hospital Pharmacy, vol. 43, Jun. 1986, pps. 1454–1461.

Marcinko, *Gentamicin–Impregnated PMMA Beads: An Introduction and Review*, The Journal of Foot Surgery, vol. 24, No. 2, 1985, pps. 116–121.

Seligson, *Grand Rounds—Antibiotic–Impregnated Beads in Orthopedic Infectious Problems*, Journal of the Kentucky Medical Association, Jan. 1984, pps. 25–29.

Schneider et al, *Use of Antibiotic–Impregnated Polymethyl Methacrylate for Treatment of Open Radial Fracture in Horrse*, Scientific Reports, JAVMA, vol. 207, No. 11, Dec. 1, 1995, pps. 1454–1457.

*Primary Examiner*—James O. Wilson
*Assistant Examiner*—Devesh Khare
(74) *Attorney, Agent, or Firm*—Nixon & Vanderhye PC

(57) ABSTRACT

This invention relates generally to the production and use of inorganic-polymer complexes for the controlled release of compounds including medicinals. Advantageously, the inorganic used is calcium sulfate.

8 Claims, No Drawings

INORGANIC-POLYMER COMPLEXES FOR THE CONTROLLED RELEASE OF COMPOUNDS INCLUDING MEDICINALS

This application is a division of application Ser. No. 09/509,016, filed Mar. 21, 2000, which was an A371 U.S. national phase application based on PCT Application No. PCT/US98/19528, filed Sep. 22, 1998, which in turn was a continuation-in-part of application Ser. No. 08/935,300, filed Sep. 22, 1997, now U.S. Pat. No. 6,391,336, the entire content of which is hereby incorporated by reference in this application.

FIELD OF THE INVENTION

This invention relates generally to the production and use of inorganic-polymer complexes for the controlled release of compounds including medicinals.

BACKGROUND OF THE INVENTION

Systemic antibiotic treatment is often unsatisfactory in cases of osteomyelitis as well as infections in devitalized tissue, avascular scar tissue, and other areas with insufficient blood supply. Increasing blood levels of antibiotics can result in toxicity. For example, aminoglycosides can produce ototoxicity and nephrotoxicity. Another problem with long-term systemic treatment with antibiotics is the selection of drug-resistant mutants. In poorly vascularized areas, the infectious organism may encounter concentrations below the minimum lethal concentration which provides the opportunity for selection of a resistant form. Also in large-animal veterinary practice, the cost of the antibiotic for systemic use can be an issue.

Antibiotic formulations of polymethylmethacrylate have been employed as antiseptic bone cement and as beads either free or attached to a wire which is used for percutaneous removal [H. W. Bucholz. et al, *Chiburg.* 43, 446 (1970)]. PMMA is not bio-erodible.

An alternative is plaster of Paris (POP) which has been used without matrix biopolymers or medicinal complexing agents as $CaSO_4 1/2H_2O$ [D. Mackey, et al, *Clin. Orthop.* 167, 263 (1982); and G. W. Bowyer, et al, *J. Trauma*, 36, 331 (1994)]. Polymethylmethacrylate and POP have been compared with regard to release profiles. Release rates from POP tend to be very fast.

Both polymethylmethacrylate and POP can be used to produce dimensionally stable beads and other structures. The acrylate cements or beads are formed by mixing pre-formed polymethylmethacrylate polymer, methylmethacrylate monomer, and a free-radical initiator. An exothermic reaction ensues which results in matrix temperatures as high as 100° C. Many antibiotics such as polymyxin and tetracycline are inactivated by these conditions [G. J. Popham, et al, *Orth. Rev.*, 20, 331 (1991)]. As mentioned above, polymethylmethacrylate is biocompatible but not resorbable. Therefore, beads used to treat local infection must be retrieved by surgery which is accompanied by the risk of reinfection.

POP beads or pellets are resorbable but show inferior drug release profiles [G. W. Bowyer, et al, *J. Trauma*, 36, 331 (1994)].

Compositions containing hyaluronic acid have been used for topical administration of pharmacological substances [F. Della Valle, et al, U.S. Pat. Nos. 5,166,331 and 4,736,024].

OBJECTS OF THE INVENTION

It is an object of the invention to provide a safe resorbable delivery system which enables controlled release of medicinals.

It is an object of the invention to provide a delivery system with controllable setting time.

It is a further object of the invention to provide a delivery system which is an injectable liquid which solidifies in a timely way once in place.

SUMMARY OF THE INVENTION

The subject invention relates to a delivery system comprising:
 a) an inorganic compound capable of undergoing hydration and/or crystalization, and
 b) a matrix polymer, and/or
 c) a complexing agent.

In another embodiment, the system comprises a complexing agent and a medicinal. Included within the invention are methods of producing sustained release of a medicinal in a mammal by administering the system with a medicinal to a mammal. A still further embodiment of the invention is a method of diagnosing disease in a mammal by administering a radiopaque matrix to the mammal.

DETAILED DESCRIPTION OF THE INVENTION

The subject invention relates to a resorbable matrix with favorable release kinetics. Inorganic compounds such as $CaSO_4 . 1/2H_2O$ can be combined with biopolymer in the presence of a bioactive agent including medicinals to produce a matrix.

In addition to the inorganic compound there are:
 (i) a matrix polymer, and/or (ii) a complexing agent. As used herein, the term "matrix polymer" refers to a polymer (often a biopolymer) which serves to control the erosion rate, setting time, and influences the release profile by raising the viscosity of the medium in the pores and channels of the delivery system. As used herein, the term "complexing agent," refers to an agent (often a biopolymer), which is used to form a salt or conjugate with the active agent which in effect raises the molecular weight of the active agent and lowers its rate of efflux. The complexing agent is typically a small molecule capable of aggregation which has affinity for the active agent. Pharmacologically acceptable hydrophobic medicinal complexing agents include proteins such as albumin, lipids or cyclodextrins which can be used to complex neutral medicinal molecules or charged molecules which contain an apolar moiety. Liposomes containing a medicinal can be entrapped within the calcium sulfate matrix.

The reaction scheme for forming a matrix including a medicinal is shown below:

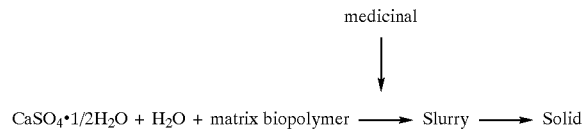

The consistency and viscosity of the slurry is dependent on the amount and nature of the matrix biopolymer. The slurry can be injected with subsequent formation of a solid in vivo.

A medicinal can exist in the inorganic-biopolymer complex either free or complexed to the medicinal complexing agent. The free compound is released relatively fast. The complexed medicinal is released relatively slowly often contingent on the bio-erosion of the inorganic-biopolymer complex. Antibiotics and local anesthetics are used to illustrate this principle:

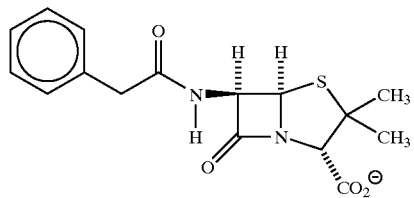

β-lactam antibiotic

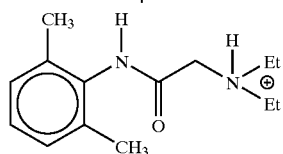

Lidocaine

The resorbable inorganic-biopolymer complex can contain free antibiotic (e.g., as the sodium salt) or in the form of a biopolymer complex with a polycation such as a polypeptide such as polymyxin B or an aminoglycoside. Lidocaine is conveniently employed as the hydrochloride, the free base, or complexed as the salt of chondroitin sulfate or polyglutamate.

I. General Considerations

The delivery system of the subject invention for use with medicinals must meet the following requirements:

1. Safety—non-toxic, non-immunogenic, non-pyrogenic, non-allergenic.
2. Resorbability—all components should be either assimilable or readily excreted.
3. Stability—the matrix should be sterilizable and precursors should have an acceptable shelf-life. Cast forms should be dimensionally stable.
4. Compatibility—the materials and the preparative conditions should not alter the chemistry or activity of the medicinal.
5. Programmability—the residence time and release profile should be adjustable.

There are typically two or three components in the inorganic-polymer complex matrix—

1. An inorganic compound, for example, $CaSO_4 \cdot 1/2H_2O$
2. Matrix polymer, for example, hyaluronic acid or dextran
3. Complexing agent, for example, chondroitin sulfate, cationic polypeptide, or cyclodextrin.

Inorganic Compounds

Calcium sulfate $.1/2H_2O$ (hemihydrate) is the preferred inorganic component. The hemihydrate takes up water and crystallizes as the higher hydrate. Unadulterated calcium sulfate matrix exhibits poor drug release profiles. With matrix polymers and complexing agent-active agent complexes the release profiles are improved. Other inorganics may be employed such as calcium silicates, aluminates, hydroxides and/or phosphates (see pages 72, 95, 327 in Reference Book of Inorganic Chemistry (1951) Latimer, W. H., and Hildebrand, J. M., Macmillan, New York, hereby incorporated by reference in its entirety).

The inorganic compound goes from slurry to solid in a reasonable time period, i.e., 10 minutes-two hours. The matrix biopolymer influences the setting time and the release profile. Sodium salts and chloride ion act as inhibitors. Sulfate salts and calcium salts accelerate the solidification process. Calcium pentosan polysulfate containing slurries solidify faster than those containing sodium as the counterion.

In an advantageous embodiment, the matrix has a porosity sufficient to permit the influx of cells (e.g., osteocytes). See Example 15.

Polymers

In order to slow the efflux of active agent, e.g., medicinal, from the dosage form, polymers, often biopolymers, are included in the matrix to raise the viscosity. Hyaluronic acid (e.g., 1–5%), proteins, e.g., collagen (gelatin), fibrinogen, which form viscous solutions (e.g., 1–30%), and dextran (e.g., 1–50%) are examples. Viscosity can be changed as a function of time. Hydrolytic enzymes such as a protease, can be included to lower the viscosity as a function of time to speed the efflux and compensate for the decrease in the medicinal gradient. This feature provides for a desirable release profile. For medicinal uses, biopolymers (polymers of biological origin) are advantageously employed.

Complexing Agents

To make biopolymer-medicinal complexes for use in parenteral matrices, polymers which are known to be safe are employed. Polymers useful for this purpose include, but are not limited to, the following:

glycosaminoglycans such as chondroitin sulfate, hyaluronic acid
polynucleotides
acidic proteins
polyglutamic acid
polyaspartic acid
pentosan polysulfate
dextran sulfate The polymers should be assimilable for use in veterinary or human medicine.

In another embodiment, lower molecular weight compounds can be used as the complexing agent. For example, carboxylic acids such as caprylic acid, undecylenic acid, piperacillin, penicillin V, nafcillin or cefazolin.

For the complexation of anionic medicinals such as some β-lactam antibiotics advantageous polymers include polypeptide cations such as polymyxins and aminoglycoside antibiotics such as amikacin. For medicinals not carrying a net positive or negative charge or those that possess a significant amount of apolar character, neutral complexing agents are employed. Examples include cyclodextrins, Polysorb 80 and proteins which bind the medicinals. Small molecules which aggregate and bind the medicinals are alternatives. Apolar molecules which form multi-molecular aggregates can be employed. This type is exemplified by liposomes. A series of active medicinals which possess varying degrees of apolar character can be advantageously employed with the apolar complexing agent. Such a series is exemplified by hydrocortisone hemisuccinate-sodium, hydrocortisone, hydrocortisone acetate, and hydrocortisone octanoate.

The rationale for using complexing agents is based on Stokes law:

$$D \propto 1/Mv$$

D=the diffusion coefficient
M=the molecular weight of the medicinal
v=the viscosity of the medium Use of complexation biopolymers in effect, raises the molecular weight of the medicinal. The presence of both the matrix biopolymer and medicinal complexing agent can increase the viscosity within the matrix which lowers the diffusivity. Another view of the retardation of release concerns the maintenance of electrical neutrality. In order for the charged medicinal to diffuse away from the medicinal complexing agent an external counterion must first diffuse into the matrix and exchange for the medicinal.

The medicinal complexing agent serves to delay the release of the medicinal. The medicinal complexing agents can be in the form of a cationic polymer such as polypeptide cations, aminoglycosides, an anionic polymer such as chondroitin sulfate and a neutral compound such as cyclodextrin or a lipid or mixture of lipids. Also, chondroitin sulfate and other polyanions can be used with a tetramethyl-lysine linker.

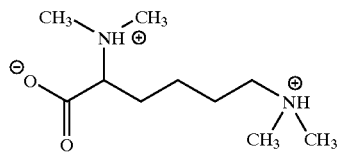

which is used in anhydride linkage with β-lactam antibiotics (I) or a carboxylated NSAID (II):

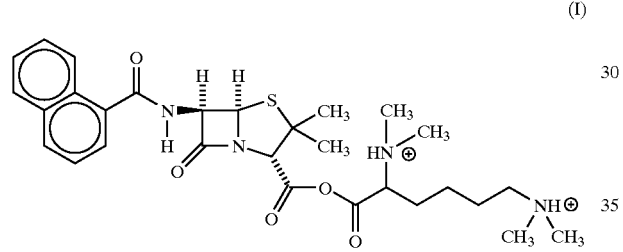

Nafcillin Complex

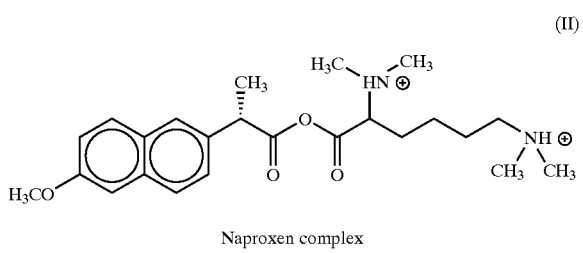

Naproxen complex

Use of a series of medicinal complexing agents of varying size is illustrated by the example of penicillin G ionically complexed to progressively larger amines: procaine, benzathine, polymyxin, and other polypeptide cations. Cationic medicinals may be analogously bound to progressively larger carboxylate (sulfate) containing compounds. An enzymatic digest of chondroitin sulfate constitutes a random series of sizes and is conveniently prepared.

In one embodiment of the invention, there is a complexing agent and a medicinal only (without an inorganic): see e.g., Table 1 compositions E, H, J, K, L and O. In another embodiment of the invention, there is a matrix polymer and a medicinal only (without an inorganic), for example, hyaluronic acid and a medicinal such as an antibiotic or anesthetic. Complexing agents for non-medicinals are discussed in section V "Non-medical Applications."

Advantageous delivery systems of the invention are shown in Table 1 below:

TABLE 1

| Formulation | CaSO$_4$ 1/2H$_2$O | Matrix polymer | Complexing agent | Medicinal |
|---|---|---|---|---|
| A R/100 mgIa | 1 g | HA - 0.6 ml (2%) | | 50 mg NF |
| B R/100 mgIa | 1 g | Dextran - 0.6 ml (20%) | lecithin - 100 mg | 50 mg NF |
| C | 1 g | HA, 0.6 ml (2%) | polyglutamic acid | 100 mg lidocaine |
| D | 1 g | HA, 0.6 ml (2%) | chon S | 100 mg amikacin |
| E | — | HA, 0.6 ml (2%) | chon S | Amikacin 100 mg |
| F | 1 g | Dextran - 6 ml (20%) HA, 0.6 ml (2%) | polymyxin | Cef 100 mg |
| G | 1 g | HA, 0.6 ml (2%) | | 500 mg HC (10% a.i.) |
| H | — | HA, 0.6 ml (2%) | | 500 mg HC (10% a.i.) |
| I | 1 g | HA, 0.6 ml (2%) | | 50 mg cis-platin |
| J | — | HA, 0.6 ml (2%) | chon S | Lidocaine 100 mg |
| K | — | HA, 0.6 ml (2%) | chon S | Morphine 100 mg |
| L | — | HA, 0.6 ml (2%) | chon S | Hydromorphone 100 mg |
| M | 1 g | HA, 0.6 ml (2%) | | 50 mg Imip |
| N | 1 g | HA, 0.6 ml (2%) | | 5 mg BMP-2 |
| O | — | HA, 0.6 ml (2%) | polymyxin | 100 mg Imip |
| P | 1 g | — | 0.6 ml chon S | lidocaine 24 mg |
| Q | .5 g | HA, 1 ml (2%) | | HA |
| R* | 1 g | Dextran 200 mg (solid) | — | Lidocaine 100 mg (solid) |
| S | 1 g | Gelatin (10%) 0.6 ml | — | Lidocaine 100 mg (solid) |

R = radiopaque

TABLE 1-continued

| Formulation | CaSO₄ 1/2H₂O | Matrix polymer | Complexing agent | Medicinal |
|---|---|---|---|---|

Ia = iodipamide
HA = hyaluronic acid, sodium salt
NF = norfloxacin
Imip = imipenem
Cef = cefazolin
HC = hydrocortisone in CD
CD = 2-hydroxypropyl-(3-cyclodextrin)
Chon S = chondroitin sulfate
LD = lidocaine
*Slurry is made with 0.6 ml of water.

II. Production of the Inorganic-Biopolymer Complex-Medicinal Matrix and Modes of Administration The basis for formation of the inorganic-biopolymer complex matrix can be expressed in the following reaction:

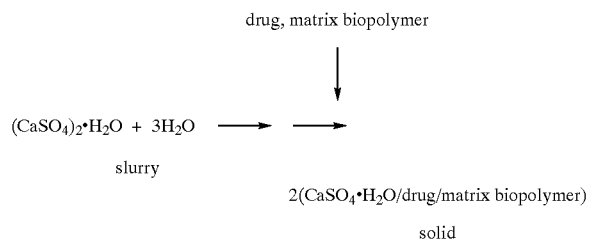

The drug, free and complexed to a medicinal complexing agent, is conveniently mixed with calcium sulfate as a finely ground solid. The matrix biopolymer is included to influence the setting time and the drug release profile.

The setting time can be adjusted so that the user can administer the inorganic-biopolymer complex matrix in the form of a liquid using a syringe with a 23 gauge needle or larger. The matrix will solidify soon thereafter. It is convenient to transfer the slurry to the barrel of a syringe using a spatula or second syringe. The plunger is inserted and the inorganic-biopolymer complex matrix is injected after expulsion of air. Salts of fatty acids can be included to facilitate release from the mold. e.g., 1–3% calcium stearate. Subcutaneous injections are routinely done with a syringe fitted with a 25-gauge needle. Dispensing into molds can be accomplished using a syringe fitted with a blunt needle or in some cases a pipette. The liquid injection can be s.c., i.m., or i.p. Advantageously, the administration is done by parenteral injection.

Administration of the solid matrix can be by surgical implant, oral, i.p., i.a. or p.a. Specific sites can be targeted for administration of the medicinal such as an anesthetic or anti-inflammatory.

The drug is conveniently employed as a solid which can be finely ground and mixed with the calcium sulfate. The matrix polymer is routinely used as a solution. In a representative formulation the following proportions and ingredients are used:

| Ingredient | Amount |
|---|---|
| Calcium sulfate | 1 g |
| Drug | 50 mg |
| matrix biopolymer at 2% | 0.6 ml |

If the calcium sulfate amount is set at 1 g, the amount of drug used is in the range of 1–200 mg and the matrix biopolymer in the range of 0.4–3 ml. The concentration of the matrix biopolymer ranges from 0.1–50%.

Cooling of the ingredients prior to mixing slows the reaction. Increased liquid/solid ratios tend to slow the reaction also. Low molecular weight alcohols, such as propanol and butanol, significantly prolong the setting time. The influence of two matrix biopolymers is shown in Table 2.

Polyethylene glycols (PEGs) can be used to suspend medicinals and calcium sulfate. The solidification is retarded by PEG. Chloride and sodium salts also inhibit solidification. Availability of water also is used as a means to control the rate of solidification. Silver sulfadiazine cream solidifies underwater. The isopropanol diffuses out and water diffuses in where it reacts with calcium sulfate-hemihydrate which results in hardening. The resultant material then slowly releases the medicinal. See Example 11. Topical formulations permit selection of a complexing agent and/or matrix polymer of non-biological origin. Examples include polyethyleneglycol (PEG) and polyvinylpyrrolidone (PVP).

TABLE 2

Change of setting time by matrix biopolymers

| Calcium sulfate | HA (%) | Setting time (min) |
|---|---|---|
| A. Hyaluronic acid (HA) | | |
| 1 g | 0.6 ml (0) | 75 |
| 1 g | 0.6 ml (.2) | 60 |
| 1 g | 0.6 ml (2) | 20 |

| Calcium sulfate | Dextran (%) | Setting time (min) |
|---|---|---|
| B. Dextran | | |
| 1 g | 0.6 ml (0) | 75 |
| 1 g | 0.6 ml (10) | 15 |
| 1 g | 0.6 ml (20) | 25 |
| 1 g | 0.6 ml (50) | 80 |

Dextran (clinical grade) is a convenient accelerator at low concentrations. The solutions are less viscous than HA solutions and dextran is inexpensive.

The inorganic-biopolymer complex can be formed as spheres, granules, cylinders, tablets and beads (including microbeads) for injection or for use in capsules. The latter can be formed by dispersing the slurry into a rapidly stirring water-immiscible medium. The size of the beads can be determined by the amount and nature of the surfactant and the stirring rate. Milling and sieving to produce beads (30–60 μ) is an alternative approach. For orthopedic and dental use the inorganic-biopolymer complex matrix can be molded and or carved into specific shapes to conform to voids in bone structures. Just prior to formation of the intractable solid, the material is plastic and can be conveniently shaped to fit openings of irregular geometry.

III. Release Profile

An idealized release profile has three phases. The burst phase is not necessary for many drugs but would be advantageous for anesthetics and antimicrobics. The maintenance, or zero-order phase, is a desirable result of the delayed release of the complexed drug. The drop-off, referred to as the closing phase, occurs as the bioerosion process comes to a conclusion. Sub-batches of beads of varying size, drug load, and release profile can be blended to provide the desired release profile.

With regard to control of the release profile, one should consider that the rate of diffusion is given by $$\text{rate}=DA(d[m]/dx) \quad (1)$$

D=the diffusion coefficient
A=the surface area
d[m]/dx=the medicinal gradient
Also, according to Stokes Law $$D \propto 1/Mv \quad (2)$$

D=diffusion coefficient
M=molecular weight
v=viscosity

The use of the medicinal complexing agent will change the effective molecular weight of the medicinal. The matrix density and composition will influence the internal viscosity of the delivery system.

Simultaneous use of medicinal complexing agents of varying size is used advantageously. For example, penicillin G in the form of salts of potassium, procaine, polymyxin, and aminoglycosides such as amikacin can be used. Polyanions with a range of sizes can be produced by enzymatically digesting glycosaminoglycans.

The shape of the delivery device will dictate the surface area. For example the surface area of a sphere is given by $$A=4\pi r^2 \quad (3)$$

The volume of a sphere is given by $$V = \frac{4\pi r^3}{3} \quad (4)$$

Combining (3) and (4) gives $$A/V=3/r \quad (5)$$

According to equation (5) as beads get smaller, the surface area per a given volume of inorganic-biopolymer complex increases. One cc of inorganic-biopolymer complex matrix dispersed as small beads delivers drug faster than one cc dispersed as large beads. The desired zero-order release profile can be approached by using the proper blend of beads of varying size.

Residence time in vivo and bio-compatability have been assessed using hamsters. Inorganic-biopolymer complex matrices were injected (0.3 ml) subcutaneously. At timed intervals the animals were sacrificed to determine the residence time and the condition of the injection site as judged by histo/path analysis. All formulations were very well tolerated. The proportion of calcium sulfate or density was an important factor in residence time. Denser formulations lasted longer. Calcium sulfate/HA (3/2) show a residence time of 35 days. Calcium sulfate/HA (1/2) showed a residence time of 20 days. Spherical beads (3.2 mm in diameter) made of calcium sulfate/HA (1/1) lasted ten days. Beads containing silver benzoate lasted two weeks and were well tolerated with no toxicity to local tissues.

Another means to control the release profile involves drug precursors. As the precursor is converted to the native compound, its avidity (affinity) for the medicinal complexing agent decreases which in turn raises its diffusivity, thus creating a biphasic release profile. As opposed to release of a molecule that is covalently linked to a polymer, this embodiment is dependent on a change in polarity. Consider the following:

Compound I is positively charged at physiological pH. It is strongly bound to chondroitin sulfate. As it hydrolyzes to form Compound II, the net charge becomes zero and as a consequence the release is accelerated. A biphasic release profile is the result when free II is included in the dosage form. The release profile can be controlled by the nature of the hydrolyzable group attached to the carboxyl group. The hydrolyzable group can be an ester, an anhydride or other labile functionalities.

IV. Medicinals

A. Non-protein Drugs

The delivery systems described herein are well suited for sustained release of: an analgesic, an anesthetic, an anti-addictive preparation (e.g., naltrexone), an anti-microbic, an antiseptic (e.gs. silver ion, and silver sulfadiazine, calcium peroxide, calcium hypochlorite), an anticoagulant, an antineoplastic, an antidepressant an anti-diabetic agent, an antihypertensive drug, an anti-inflammatory agent, an antinauseant, an anorexic, an antiulcer drug, a cardiovascular drug, a chondroprotective agent, a contraceptive, an antihistamine, a diuretic, a hormone/antihormone, an immunosuppressive, a narcotic detoxification agent, a uricosuric agent, and a wound healing promoter.

A logical alternative to systemic treatment is to employ delivery systems for local release of antibiotics. In this case, levels much greater than the minimum lethal concentration can be achieved in the therapeutic compartment while blood levels remain low. Inorganic biopolymer complexes can be implanted as beads after surgical debridement or the matrix can be injected as a liquid with subsequent solidification.

The inorganic-biopolymer complexes containing antibiotics are especially useful in filling cavities in bone produced by osteomyelitis. Placement of antibiotic-inorganic-biopolymer complexes in the vicinity of infected bone or other tissue results in eradication of the micro-organism and permits aseptic healing accompanied by resorption of the inorganic-biopolymer complex. When treating bone lesions, bone morphogenic proteins can also be included to promote growth of new bone.

Inorganic biopolymer complexes are effective for treatment of other local infections, such as joint sepsis, surgical infections, wound infections, uterine infections, oral-dental-periodontal infections, vaginitis, and localized abscesses. Likely infectious agents include Aeromonas, Capnocytophaga, Citrobacter, Clostridium, Edwardsiella, Eichenella, Enterobacter, Enteroccus, E. Coli. Fusobacterium, Hafnia, Kingella, Klebsiella, Moraxella, Morganella, Mycobacterium, Pasturella, Peptostreptococcus, Plesimonas, Proteus, Pseudomonas, Staphylococcus, Streptococcus, and Vibrio.

An advantageous antimicrobic for treatment of localized infections has the following characteristics:

1. Cidal
2. Broad spectrum
3. Non-toxic to local tissues
4. Soluble and mobile, that is, readily crosses inflamed membranes.

Antiinfectives of special interest include gentamicin, clarithromycin, minocycline and lincomycin, amikacin, penicillin, cefazolin, ciprofloxacin, enrofloxacin, norfloxacin, silver sulfadiazine, imipenem, piperacillin, nafcillin, cephalexin, vancomycin, nystatin, and amphotericin B or salts thereof. Salts of amikacin-piperacillin and amikacin-caprylic acid are useful in that they provide slower release. Further, amikacin acts synergistically with piper-acillin and other β-lactams.

In high risk surgical procedures, the antibiotic inorganic-biopolymer complexes can be used prophylactically. In abdominal surgery antibiotic beads can be distributed to provide antibiotic coverage at critical points. Placing antibiotic beads under the incision is often advantageous.

Chondroprotective agents such as chondroitin sulfate, hyaluronic acid, pentosan polysulfate and dextran sulfate can also be used, optionally with an antiinfective.

Inorganic biopolymer complexes for local delivery of anti-inflammatory drugs hold great promise for treatment of osteoarthritis, degenerative joint disease, and other such afflictions. Neutral and charged forms are advantageously employed together. For example, free hydrocortisone and hydrocortisone succinate complexed to polymyxin is a useful combination. The anti-inflammatory inorganic-biopolymer complexes are placed adjacent to diseased joints, tendon sheaths, etc. Use can accompany arthroscopic procedures both as an injectable and as pre-formed implants. NSAIDs are also of interest including naproxen, and disalicylate, NSAIDS, e.g., analgesics such as aspirin, and other medicinals can be formulated in tablet or capsule form for oral administration.

Inorganic-biopolymer complexes for pain control are primarily based on free and complexed cationic anesthetics such as lidocaine, buvicaine, bupivacaine, chloroprocaine, procaine, etidocaine, prilocaine, dezocine, hydromorphone, etc. An advantageous medicinal complexing agent is chondroitin sulfate. Tablets or beads are especially useful following arthroscopic procedures. Implants are placed next to the joint capsule laterally and medially. Pain relief is provided for 3–5 days which obviates or greatly reduces systemic use of narcotics.

In conjunction with surgical and diagnostic procedures, analgesia and tranquilization can be provided by the use of a complex of chondroitin sulfate and two bio-active compounds—fentanyl and droperidol. The simultaneous use of free and bound forms of the active agents provides rapid onset of the desired effects followed by sustained release from the polymeric salt.

Antineoplastics such as ifosfamide, cytoxan, carboplatin, cis-platin, leuprolide, doxorubicin, carmustine, bleomycin, and fluorouracil can be formulated in inorganic-biopolymer complexes for regional chemotherapy. In situations in which locally disseminated tumor is discovered and surgical removal is deemed inadvisable, administration of inorganic-biopolymer complex via injection is advantageous. Charged agents can be employed as salts with medicinal complexing agents as well as free. Neutral molecules can be formulated with cyclodextrins and emulsifiers. Also, following resection, antineoplastic inorganic-biopolymer complexes can placed in the void left by the tumor as a preventative of recurrence.

Radiopaque inorganic-biopolymer complexes can be produced by inclusion of $BaSO_4$, iodipamide, or other imaging agents in the complex. These formulations can be readily visualized radiographically during and after surgical procedures.

Pre-formed beads and tablets can be used as prophylactic anti-infectives and as pain control agents. These inorganic-biopolymer complexes are especially useful at the conclusion of orthopedic procedures such as joint arthroscopy and arthroplasty.

B. Medicinal Proteins

As used herein, the term "medicinal" includes proteins as well as small molecules. The term "protein" includes naturally occurring proteins, recombinant proteins, protein derivatives, chemically synthesized proteins, and synthetic peptides. Medicinal proteins useful in the subject invention include colony stimulating factors (CSF) including G-CSF, GM-CSF, and M-CSF; erythropoietin; interleukins, IL-2, IL-4, IL-6, etc; interferons; growth factors (GF) including epidermal-GF, nerve-GF; tumor necrosis factor (TNF); hormones/bioactive peptides; ACTH; angiotensin, atrial natriuretic peptides, bradykynin, dynorphins/endorphins/β-lipotropin fragments, enkephalin; gastrointestinal peptides including gastrin and glucacon; growth hormone and growth hormone releasing factors; luteinizing hormone and releasing hormone; melanocyte stimulating hormone; neurotensin; opiode peptides; oxytocin, vasopressin and vasotocin; somatostatin; substance P; clotting factors such as Factor VIII; thrombolytic factors such as TPA and streptokinase, enzymes used for "replacement therapy," e.g., glucocerebrosidase, hexoseaminidase A; and antigens used in preventative and therapeutic vaccines such as tetanus toxoid and diptheria toxoid. Medicinal proteins of special interest appear below:

| Medicinal | Clinical Indication |
| --- | --- |
| G-CSF | Adjunct to myelosuppressive chemotherapy |
| Erythropoietin | Anemia, kidney disease |
| "Replacement" enzymes | Heritable genetic deficiencies of enzymes |
| Hormones | endocrine gland failure, treatment of hormone sensitive cancers, contraception, growth promotion |
| Cytokines such as colony stimulating factors, e.g., GM-CSF, interferons, e.gs., IFN-alpha, IFN-beta, interleukins, e.gs., IL-1, IL-2 and IL-6 and TNF | Immunoadjuvants |

-continued

| Medicinal | Clinical Indication |
|---|---|
| Vaccine antigens | Immunization-preventative and therapeutic |
| BMP-2 | Bone replacement |
| Wound healing promoters | burns, trauma |
| rh-Lysozyme | antimicrobic |
| Growth Factors | growth promotion |

Inhibitors/antagonists of the above

V. Non-medical Applications

There are agricultural and industrial applications of the matrices of the invention. The polymers are not necessarily of biological origin. For example, the matrix polymer can be selected from the following: polyethyleneglycol, polyvinylpyrrolidone, polyvinylalcohol, starch, xanthan, cellulose and cellulose derivatives (e.g., carboxymethylcellulose). Examples of non-ionic complexing agents include polyoxyethylene esters and ethers, and surfactants of either biological or non-biological origin. Examples of ionic complexing agents include polyacrylic acid, alginic acid, dextran sulfate, polyvinylpyridine, polyvinylamine, polyethyleneimine as well as synthetic lipid compounds.

Examples of bioactive compounds which can be used with the matrix of the invention include sterilants, pheromones, herbicides, pesticides, insecticides, fungicides, algicides, growth regulators, nematicides, repellents, and nutrients.

The following Examples are illustrative, but not limiting of the compositions and methods of the present invention. Other suitable modifications and adaptations of a variety of conditions and parameters normally encountered which are obvious to those skilled in the art are within the spirit and scope of this invention.

EXAMPLES

Example 1
Preparation of a Radiopaque Norfloxacin-inorganic-biopolymer Complex $CaSO_4.1/2H_2O$ is sterilized by heating at 120° C. for 4 hours and then divided into 1 g aliquots which are stored in individual plastic containers in a desiccator. Calcium sulfate(1 g), 50 mg norfloxacin, and 110 mg iodipamide, all finely ground, are mixed thoroughly. To this mixture is added 0.6 ml of cold hyaluronic acid solution (2%). The slurry is mixed to an even consistency and is loaded into the barrel of a 3 ml syringe with a spatula. The plunger is replaced and the air expelled. The needle is attached to the syringe and the inorganic-biopolymer complex is ready for administration or casting in a mold.

Example 2
Preparation of Lidocaine Matrix

Calcium sulfate-hemihydrate (1 g) was mixed with finely ground dextran (clinical grade, 0.2 g) and lidocaine (0.1 g). The solid mixture was then stirred with 0.6 ml of water or alternatively 0.6 ml of HA (2%). The slurry was apportioned into screw-cap vials, 0.2 ml each. After 24 hr. at room temperature the samples were refrigerated. The release experiments were done at 37° C. using 1 ml of buffer per vial with changes at 24 hr. intervals. The release buffer was PBS containing 0.1% sodium azide. The concentration of lidocaine was determined spectrophotometrically (260 nm). See Table 3 below

TABLE 3

Release of Lidocaine for Matrices with (B) and without (A) the Matrix Biopolymer.

| Matrix A | | Matrix B (11% Dextran) | |
|---|---|---|---|
| Day | % Release | Day | % Release |
| 1 | 85 | 1 | 24 |
| 2 | 10 | 2 | 26 |
| 3 | 1 | 3 | 22 |
| 4 | 1 | 4 | 15 |
| 5 | 1 | 5 | 6 |

Example 3
Preparation of an Inorganic-biopolymer Complex Containing Bound and Free Amikacin Chondroitin sulfate solution (sodium salt, 5%) is converted to the acid form by passage over a column of Dowex-50. Assuming a residue molecular weight of 500, a stoichiometric amount of amikacin free base is added at 0–4° C. The pH is adjusted to 7 and the product is frozen. Alternatively, the product is freeze-dried and stored in a desiccator. Using chondroitin sulfate as the medicinal complexing agent, other complexes can be made by this procedure. Lidocaine, morphine, entamicin, clindamycin, and doxorubicin are examples.

Calcium sulfate (1 g) is thoroughly mixed with 50 mg of chondroitin sulfate-amikacin (above) and 25 mg amikacin sulfate(1:2). Hyaluronic acid solution (0.6 ml, 2%) is added and the mixture handled as described in Example 1.

Example 4
Preparation of Cis-platin Beads

Calcium sulfate (1 g) is mixed with 50 mg of finely ground cis-platin (cis-diaminedichloroplatinum). To this mixture 0.6 ml of hyaluronic acid solution (2%) is added and the slurry is transferred to a 3 ml syringe as described in Example 1. Using a 20-gauge blunt end needle, the inorganic-biopolymer complex is injected into a teflon mold with spherical holes which are 3.2 mm in diameter. After 48 hours at room temperature, the mold is split and the beads are removed with a dental explorer under sterile conditions. Beads are placed in slits made surgically around a tumor or around the site of tumor removal in an effort to prevent recurrence.

Example 5
Preparation of Cefazolin-inorganic-biopolymer Complex

Polymyxin sulfate solution (10%) is cooled to 0–4° C. A stoichiometric amount of barium hydroxide solution is added to produce the free base of polymyxin and insoluble barium sulfate. Four equivalents of cefazolin, dissolved in 50% THF, are added. After trituration, the suspension is filtered to remove the barium sulfate. The residue is washed to recover all of the conjugate. The solvent of the combined filtrate and washing is evaporated and the polymyxin-cefazolin salt is used as the solid. Calcium sulfate (1 g) is mixed with 100 mg of polymyxin-cefazolin salt and 50 mg of cefazolin-sodium. To this solid mixture is added 0.6 ml of hyaluronic acid (2%). The slurry is administered directly or placed in a bead or tablet mold. Other basic polypeptides, or aminoglycosides may be used in place of polymyxin.

Example 6
Penicillin G-inorganic-biopolymer Complex

Penicillin G is employed simultaneously as the salt of potassium, procaine, benzathine, and polymyxin. To 2 g of calcium sulfate is added 100 mg of penicillin G-potassium plus 100 mg procaine-penicillin and 50 mg each of polymyxin-penicillin and amikacin-penicillin. After thorough mixing, 1.2 ml of 20% dextran is added and the slurry handled as described above.

Example 7
An Anti-inflammatory Inorganic-biopolymer Complex

An apolar medicinal complexing agent such as Polysorb 80 is employed with the following forms of hydrocortisone:
A=hydrocortisone hemisuccinate-sodium
B=hydrocortisone
C=hydrocortisone acetate
D=hydrocortisone octanoate To 1 g of calcium sulfate is added 25 mg each of A, B, C, and D above. To this mixture is added 0.6 ml of 20% dextran plus 100 ul of Polysorb 80. The slurry is handled as described above.

Example 8
Herbicide (Dinoseb) Inorganic-polymer Composite

Dinoseb is conjugated with polyethyleneimine (PEI) using water as a solvent. To 1 ml of a PEI solution (10%) is added 200 mg of dinoseb and the pH is adjusted to near neutrality. This mixture (600 mg) is combined with 1 g of calcium sulfate and the slurry used to produce beads with a water-immiscible medium such as sesame oil. Naphthalene acetic acid can be used in place of dinoseb to produce a long-lasting root growth stimulator.

Example 9
Treatment of a Bone Infection

A colt, aged three months, sustained a fracture which was successfully treated surgically to the point at which an infection (Enterobacter) occurred. A matrix including norfloxacin (formulation A of Table 1) was used to treat the infection. After thorough debridement of the cavity, the void was filled with freshly prepared matrix. No surgical intervention was necessary after the treatment. The infection was eradicated and no sign of lameness appeared after 1 month.

Example 10
Preparation of the Salt, Amikacin-chondroitin Sulfate

Chondroitin sulfate (1 g) is dissolved in 4 ml distilled water at 0–4° C. TCA (1 ml ml, 32%) at 0° C. is added with stirring. The solution is poured into 20 ml of cold ethanol; the precipitate is collected on a filter, washed and dried. One equivalent of solid amikacin (free base) is added. The solution is adjusted to pH 7.4. It can be used as is or supplemented with amikacin sulfate.

Example 11
Preparation of Silver Sulfadiazine Cream—A Topical Anti-infective Component A—520 g of PEG 400 plus 200 g PEG 3350 warmed to form a single phase (40–50°).
Component B—60 g of PVP K-30 dissolved in 170 ml of anhydrous isopropanol
Component C—20 g of silver sulfadiazine (micronized) suspended in 30 ml of anhydrous isopropanol Preparation: Components A, B, and C are mixed with stirring at 45–55°. To this suspension 1 kg of calcium sulfate hemihydrate is gradually added with stirring. After mixing is complete, the product is transferred to a polypropylene vessel and stored at room temperature or below. The product is protected from light. Viscosity can be reduced by increasing the relative amount of PEG 400 with regard to PEG 3350. The converse is also true. The weight of calcium sulfate can be reduced by 50% with the other component weights held constant. The product is then packaged into 32 ml syringes with nozzle end caps and polyethylene seals.

Use: Silver sulfadiazine cream is indicated for treatment of equine thrush and white line disease. After removal of foreign matter and necrotic tissue, silver sulfadiazine cream is applied to the hoof with concentration on the cleft of the frog. For best results the syringe is used at 70–90°. The product is particularly advantageous for prophylactic use under shoes or pads at each shoeing.

Example 12
Silver Sulfadiazine Paste—A Topical Anti-infective for Equine Hoof Rebuilding Component A—Silver sulfadiazine cream (above)
Component B—2% Hydroxypropyl methylcellulose in 50% alcohol (e.g., methanol, ethanol, propanol, isopropanol)

Preparation: At 30–40° two parts of Component A are mixed with one part Component B to form a thick paste. This product is stored in closed polypropylene tubs and protected from light.

Use: Following hoof resection silver sulfadiazine paste is applied with a spatula to fill voids and reshape the hoof. It can be used under unmedicated plastic hoof rebuilders.

Example 13
Silver Sulfadiazine Beads—A Topical Anti-infective

Preparation: 1 g of calcium sulfate-hemihydrate and 75 mg of silver sulfadiazine (USP, micronized) are thoroughly mixed. A slurry is made with 0.5 ml of Solution D. The solid which forms is ground to a powder; Particle size of <50 microns works well. Solution D is 10% dextran sulfate (sodium form, USP, MW=8.000) which is sterile filtered.

Use: These beads can be used directly on open wounds. Incorporation in a non-aqueous organic ointment base is useful; white petrolatum is a good choice as is polyethylene glycol based preparations. Suspension of these beads in propylene glycol or other liquid vehicle is valuable for treatment of Otitis Externa.

Example 14
Silver Sulphadiazine Film—A Topical Anti-infective

The films are cast using 2% HPMC in 50% alcohol. The silver sulfadiazine beads (1–5% by wt.) described above are dispersed into the HPMC solution and the dispersion is poured onto a glass or plastic surface. Solvent evaporation results in a very strong film. Other film forming technologies are also applicable. These films can be incorporated into wound dressings and bandages. The film is stable in air but dissolves when in contact with water or moist tissue. Once in contact with moisture the microbeads begin releasing silver sulfadiazine, which is active against a broad spectrum of bacteria, yeast, and fungi.

Example 15
Porous Orthopedic Filler

This preparation can be used to fill extraction sockets, periodontal defects, orthopedic defects, root canals, and screw channels following fracture repair, etc. Porosity allows the penetration of cells such as osteocytes. Bioactive agents such as anti-infectives and osteogenic compounds can be included to promote bone resorption in a sterile environment as the matrix is resorbed.

Component A=$Ca(H_2PO_4)_2/NaHCO_3$ (1/1)
Component B=Calcium sulfate-hemihydrate Component C=Biopolymer solution, e.g., Solution D from Example 13

Component A (0.1–0.3 g) and Component B (0.7–0.9) are thoroughly mixed (total=1 g). This solid mixture is then blended with 0.6 ml of biopolymer solution. The slurry is immediately injected and allowed to solidify in situ. Amikacin sulfate (50–100 mg) can be included as the antibiotic.

Example 16
Preparation of Sterile Amikacin Matrix

Calcium sulfate-hemihydrate is sterilized by dry heat—120° for 4 hrs. Solution A is prepared as follows. Dextran sulfate (1 g/CAS9011-18-1) is dissolved in 10 ml of water along with 3 g of amikacin sulfate (CAS 39831-55-5). The solution is filtered (0.2 micron filter) into sterile serum cap vials. To 1 g of calcium sulfate-hemihydrate is added 0.5–0.7 ml of Solution A. The components are mixed thoroughly to produce a uniform slurry. The slurry can be injected directly into the patient, injected into a mold, or used to produce microbeads. Operations including mixing and beyond are conducted is a sterile space. Molds for 3-mm beads are sterilized by ethylene oxide treatment. Milling equipment is sterilized by autoclaving or by treatment with ethylene oxide.

Example 17
Treatment of Equine Joint Sepsis

Infection of the equine joint is characterized by heat, swelling, pain on palpation/flexion, and lameness. The use of amikacin beads is preceded by through-and-through lavage or other joint drainage/flushing technique. Amikacin beads are suspended in lactated Ringer's solution and injected, i.a., with an 18 ga needle. Dosages range from 100–500 mg. Systemic antibiotics may be used as an adjunct. Culture to show susceptibility is obviously desirable. If amikacin beads are not indicated, cefazolin matrix beads may be employed. Larger beads, 3 mm, can be placed within the joint capsule using the arthroscope or a cannula.

Represenative results with amikacin beads (100 mg) are as follows:

Case 1. Luxated LR fetlock with exposure of distal M3. Prior treatment consisting of extensive joint flushing, and systemic antibiotic treatment was unsuccessful—persistent positive cultures for Staph. and Strep. Injection of 100 mg of amikacin beads resulted in resolution of the infected condition—no more flaring, heat, or positive cultures. Horse returned to sound condition.

Case 2. Puncture wound of the RR fetlock resulted in sepsis of the tendon sheath. Surgery including annular resection systemic antibiotic therapy did not result in correcting the condition. Amikacin beads were injected and infection (Staph.) was eradicated as judged by culture and symptoms. Horse returned to sound condition.

Case 3. Puncture wound of left hock joint resulting in an infection. Horse was treated immediately with amikacin microbeads and the treatment repeated after one week. Infection was resolved; horse returned to training.

It will be readily apparent to those skilled in the art that numerous modifications and additions may be made to both the present invention, the disclosed device, and the related system without departing from the invention disclosed.

What is claimed is:

1. A method of treating bacterial infection in a mammal comprising administering to said mammal a solid composition comprising an anti-infective which is dispersed throughout a solid matrix reaction product of an aqueous mixture comprised of: a) an anti-infective selected from the group consisting of gentamicin, clarithromycin, minocycline and lincomycin, amikacin, penicillin, cefazolin, ciprofloxacin, enrofloxacin, norfloxacin, silver sulfadiazine, imipenem, piperacillin, nafcillin, cephalexin and vancomycin or salts thereof, b) calcium sulfate hemihydrate, and c) a matrix polymer.

2. A method as in claim 1, further comprising a chondroprotective agent.

3. A method of treating bacterial infection in a mammal comprising administering to said mammal a solid composition comprising an anti-infective which is dispersed throughout a solid matrix reaction product of an aqueous mixture comprised of: a) an anti-infective selected from the group consisting of gentamicin, clarithromycin, minocycline and lincomycin, amikacin, penicillin, cefazolin, ciprofloxacin, enrofloxacin, norfloxacin, silver sulfadiazine, imipenem, piperacillin, nafcillin, cephalexin and vancomycin or salts thereof, b) calcium sulfate hemihydrate, and c) a complexing agent.

4. A method of treating cancer in a mammal comprising administering to said mammal a solid composition comprising an anti-neoplastic agent which is dispersed throughout a solid matrix reaction product of an aqueous mixture comprised of: a) an anti-neoplastic agent selected from the group consisting ifosfamide, cytoxan, carboplatin, cis-platin, leuprolide, doxorubicin, carmustine, bleomycin, flourouracil, b) calcium sulfate hemihydrate, c) a matrix polymer, and/or d) a complexing agent.

5. A method of treating inflammation in a mammal comprising administering to said mammal a solid composition comprising an anti-inflammatory agent which is dispersed throughout a solid matrix reaction product of an aqueous mixture comprised of: a) an anti-inflammatory selected from the group consisting of hydrocortisone, hydrocortisone acetate, hydrocortisone octanoate, hydrocortisone hemisuccinate-sodium, hydrocortisone succinate, b) calcium sulfate hemihydrate, C) a matrix polymer, and/or d) a complexing agent.

6. A method of scaffolding bone or filling a defect in bone comprising administering to said bone a composition comprising: calcium sulfate hemihydrate; and a matrix polymer which slows the release of said active agent, wherein said composition becomes a solid matrix due to hydration of calcium sulfate hemihydrate in an aqueous mixture of said active agent, said matrix polymer and said calcium sulfate hemihydrate.

7. A method as in any one of claims 1–6, wherein the solid matrix further comprises a salt of a fatty acid.

8. A method as in claim 7, wherein the salt of a fatty acid comprises calcium stearate.

* * * * *